United States Patent [19]

Frederick et al.

[11] Patent Number: 4,874,365

[45] Date of Patent: Oct. 17, 1989

[54] FEEDING TUBE FACILITATING IMPROVED PLACEMENT AND PERMITTING SUBSEQUENT DELIVERY OF A SECOND PRESCRIBED PRODUCT AND METHOD THEREFOR

[75] Inventors: Warren P. Frederick, Wonder Lake; Sarah L. Steele, Evanston; David D. Rhodes, Palatine; Christopher L. Arns, Lake Bluff, all of Ill.

[73] Assignee: Baxter International Inc., Deerfield, Ill.

[21] Appl. No.: 659,809

[22] Filed: Oct. 11, 1984

[51] Int. Cl.[4] .......... A61M 25/00

[52] U.S. Cl. .......... 604/54; 604/165; 604/270; 604/284

[58] Field of Search .......... 604/54, 29, 95, 170, 604/280–283, 270, 77, 207.14

[56] References Cited

U.S. PATENT DOCUMENTS

| | | | |
|---|---|---|---|
| D. 233,845 | 12/1974 | Fettel | D32/1 R |
| D. 239,283 | 3/1976 | Villari | D23/19 |
| D. 251,734 | 5/1979 | McCaw et al. | D24/53 |
| 3,399,674 | 9/1968 | Pannier et al. | 604/165 |
| 3,459,183 | 8/1969 | Ring et al. | 128/214.4 |
| 3,707,972 | 1/1973 | Villari et al. | 128/349 R |
| 3,741,217 | 6/1973 | Ciarico | 128/349 |
| 3,766,916 | 10/1973 | Moorehead et al. | 128/214.4 |
| 4,000,739 | 1/1977 | Stevens | 128/214.4 |
| 4,231,367 | 11/1980 | Rash | 128/214.4 |
| 4,249,535 | 2/1981 | Hargest, III | 604/54 |
| 4,257,416 | 3/1981 | Prager | 604/80 |
| 4,326,519 | 4/1982 | D'Alo et al. | 128/214.4 |
| 4,335,770 | 6/1982 | Kulle et al. | 150/8 |
| 4,398,076 | 6/1983 | Waters | 604/165 |

*Primary Examiner*—C. Fred Rosenbaum
*Attorney, Agent, or Firm*—Kay H. Pierce; Paul C. Flattery; Brad Price

[57] ABSTRACT

A naso-gastric feeding tube (10) includes a hollow, flexible tube (12) having an open, proximal end (14) permanently secured to a hollow adapter (16), forming an integral unit. A stylet (56) is removably mounted within the stylet port (42) of the adaptor (16). A syringe (72) may be secured to the placement port (44) in order to conduct the placement confirmation test to assure proper insertion of the feeding tube within the patient, eliminating the need for removing and then reinserting the stylet to confirm proper insertion of the feeding tube (10). Additionally, the feeding tube (10) permits delivery of a second prescribed product without disconnecting the tube (10) from the source of the first prescribed product.

4 Claims, 3 Drawing Sheets

FEEDING TUBE FACILITATING IMPROVED PLACEMENT AND PERMITTING SUBSEQUENT DELIVERY OF A SECOND PRESCRIBED PRODUCT AND METHOD THEREFOR

FIELD OF THE INVENTION

The present invention relates to an improved naso-gastric feeding tube and an improved method for properly positioning the tube within a patient and for delivering two or more prescribed products to the patient.

BACKGROUND OF THE INVENTION

Naso-gastric feeding tubes, also known as enteral feeding tubes or enteric feeding tubes, are typically used to introduce nutritional substances or other prescribed products to a patient. The products are typically in a "soupy" form of liquid and solid or liquid only.

The tubes usually have a weighted distal end called a bolus, which is used to assist in placing the tube within the patient and for keeping the tube in that position once it is correctly positioned.

The proximal end of the naso-gastric tube is typically connected to an enteral administration set which in turn is connected to a container having a prescribed product therein. Such an enteral feeding container and enteral administration set are shown for example in U.S. Pat. No. 4,335,770 to Kulle et al., assigned to the assignee of the present invention. The nutrition product is then delivered to the patient through the administration set and the feeding tube.

A principal problem associated with naso-gastric feeding tubes is their proper placement within the patient. It is advantageous for the feeding tube to be quite flexible so as to cause less pain and trauma to the patient and to increase the period of time of possible intubation. To enable insertion of the extremely flexible feeding tube through the nose and down into the stomach or intestine of the patient, the tube must be made more rigid. To allow for placement of this flexible tube, a rigid wire stylet or other structure is usually employed and is removably mounted within the hollow tube, allowing the tube to be flexible but providing sufficient rigidity to insert the feeding tube into the patient. Other means for increasing the rigidity of the feeding tube are also known. The wire stylet is removed before delivery of the prescribed product so that the feeding tube will be extremely flexible for the remainder of the time it is within the patient.

One way to confirm proper placement of the distal end of the feeding tube is to take an x-ray of the tube while the stylet is still in place. This is a relatively time-consuming and expensive placement confirmation procedure and exposes the patient to x-rays. However, it has the advantage that, should placement be improper, the stylet and feeding tube may be moved together within the patient until placement is correct.

Two other more commonly used means to test for the proper positioning of the tube both require removal of the stylet after the operator believes insertion of the tube is proper. Once the stylet is withdrawn, the first procedure requires connecting a syringe to the proximal end of the feeding tube. The operator then pulls the piston to expand the syringe cylinder, attempting to withdraw some liquid from the stomach into the syringe. If liquid from the stomach is withdrawn, the operator knows that proper placement has been achieved. Alternatively, in the second procedure, once the stylet is removed, the operator secures a syringe to the proximal end of the feeding tube, as with the first procedure. The operator then forces air or other fluid out of the syringe, through the feeding tube and listens with a stethoscope for gurgling or other audible mark in the patient's stomach. Occurrence of the audible mark confirms proper tube placement.

The disadvantage with each of these two procedures is that removal of the stylet is required. If proper placement is confirmed by the test procedure, no problem is presented and the feeding tube may be connected to a source container of a prescribed product, usually by means of the above-mentioned administration set. However, the first attempt at proper feeding tube placement is often unsuccessful, which usually requires that the stylet be reinserted into the feeding tube. This is often painful to the patient and is a time consuming procedure as well. When the stylet is reinserted, the operator attempts to re-position the feeding tube. The operator then withdraws the stylet once more and performs one of the placement confirmation tests with the syringe as described above. This procedure is repeated until proper placement is confirmed.

Another problem associated with providing prescribed substances such as nutrition products to a patient through an enteral system is that the systems do not provide for the immediate addition of a second prescribed product. A second prescribed product, such as for example a drug or vitamins, may be added to the source container, such as the container shown in the above-identified U.S. Pat. No. 4,335,770. However, this means the second prescribed product will be diluted within the entire amount remaining of the first prescribed product. Furthermore, the second prescribed product will be delivered over a rather lengthy time period. The second prescribed product cannot be delivered immediately unless the feeding tube is disconnected from the source container and the second prescribed product delivered by syringe, for example, at the proximal end of the feeding tube. U.S. Pat. No. 4,388,076 discloses an intubating device with a hollow stylet plug through which fluid may pass to confirm proper tube placement while the stylet is still within the tube. However, such a structure suffers from the deficiencies of other feeding tubes in that the addition of a second prescribed product quickly and without dilution by the first prescribed product requires that the feeding tube be disconnected from the administration set and reconnected after injection of the second prescribed product. In addition, even if the operator goes to this trouble to introduce a second product, the second product cannot be delivered over an extended time period, separately from the first product.

It is apparent that there is a great need for a naso-gastric feeding tube which reduces insertion time and trauma to the patient and which allows for subsequent delivery of a second prescribed product without disconnecting the delivery system.

SUMMARY OF THE INVENTION

The naso-gastric feeding tube of the present invention solves these problems by providing a flexible tube having a discharge aperture defined near its distal end. A hollow adapter is permanently secured to the proximal end of the hollow tube. The interior of the adapter is in open communication with the hollow tube and with both a stylet port and a placement port within the adapter.

A stylet including a stylet plug removably mounted in the stylet port and a stylet wire permanently mounted to the stylet plug extends substantially the entire length of the hollow tube. The maximum exterior diameter of the stylet wire is less than the interior diameter of the hollow tube so that the placement port is always in open communication with the discharge aperture at the other end of the hollow tube. At least one of the stylet port and placement port includes closure means such as a cap associated therewith.

This unique structure solves the problems associated with feeding tubes as outlined above in accordance with the method of the invention which includes inserting the feeding tube within the patient's naso-gastric system and then, with the stylet remaining within the hollow tube, performing one of the placement confirmation tests with a syringe. The syringe is secured to the placement port with the stylet still within the hollow tube. Upon achieving a positive result to the confirmation test, the stylet is withdrawn and one of the stylet and placement port is secured to the distal end of an enteral administration set which is connected to a source of prescribed product. The other of the ports is closed with closure means. In the preferred embodiment of the invention, it is the stylet port that is connected to the administration set and the placement port is closed with the closure means.

The method of the invention further includes delivering a second prescribed product through the other of the ports, which in the preferred embodiment is the placement port, without disconnecting the delivery system.

DETAILED DESCRIPTION OF THE PREFERRED EMBODIMENT

Figure 1:
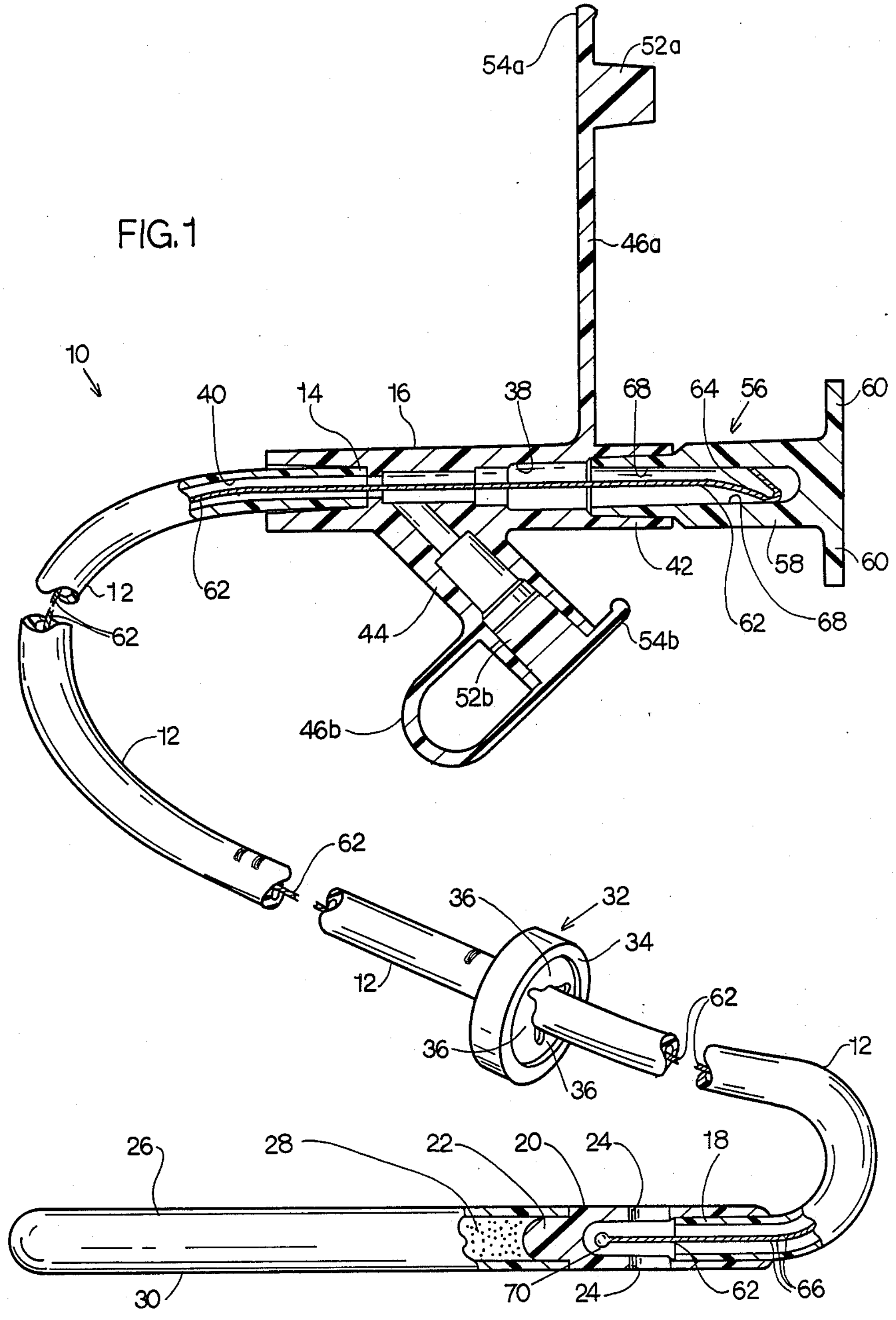
FIG. 1 is a perspective view in partial cross-section of the naso- gastric feeding tube of the present invention.
Figure 2:
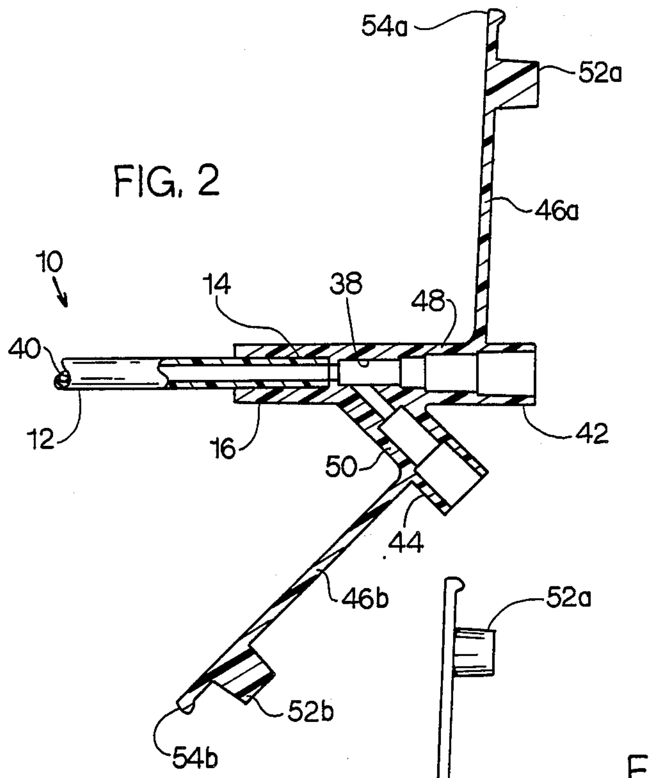
FIG. 2 is a fragmentary, cross-sectional view, illustrating the adapter with the stylet removed.

Referring to FIGS. 1 and 2, there is illustrated the naso-gastric feeding tube 10 of the invention. The feeding tube 10 includes a hollow, flexible tube 12 of a plastic material such as polyurethane. The hollow tube 12 has an open, proximal end 14 permanently secured to a hollow adapter 16, forming an integral unit.

In the preferred embodiment of the invention, the distal end 18 of the hollow tube 12 is permanently secured by adhesive or other means within a molded plastic discharge portion 20 having a closed end 22. The discharge portion 20 defines two discharge apertures 24 in the sidewall 25 of the discharge portion 20. The discharge apertures 24 are in open communication with the interior of the hollow tube 12 at the distal end 18.

The feeding tube 10 further includes a closed plastic bolus segment 26 secured about the closed end 22 of the discharge portion 20. The bolus segment 26 contains tungsten powder 28 to provide additional weight to the distal end portion 30 of the feeding tube 10. Other weighted bolus structures are of course possible. The structure of the discharge portion 20 and the bolus segment 26 are quite similar to structure illustrated in U.S. patent application Ser. No. 435,575 to Becker et al, filed Oct. 19, 1982 assigned to the assignee of the present invention.

A slidable ring 32 may be mounted about the exterior of the tube 12. The slidable ring 32 may be made of a soft resilient plastic material. The slidable ring 32 includes a thick outer wall 34 and three thin flaps 36 extending inwardly from the outer wall 34. The flaps 36 create a friction fit with the tube 12.

The interior 38 of the hollow adapter 16 is in open communication with the interior 40 of the tube 12. The adapter 16 is in the preferred embodiment a separately molded plastic piece secured to the proximal end 14 of the tube 12 by solvent bonding. The adapter 16 includes a stylet port 42 and a placement port 44.

Closure means are provided for both the stylet and placement port 42, 44 respectively. The closure means includes flexible extension arms **46*a*, 46*b* extending from the stylet port wall 48 and the placement port wall 50 respectively. Plugs 52*a*, 52*b* extend from the flexible extension arms 46*a*, 46*b* respectively near the ends 54*a*, 54*b* thereof. The plugs 52*a*, 52*b* are sized to fit snugly within and close off the stylet and placement ports 42, 44 respectively. As will be discussed below, only one of the stylet and placement ports 42, 44 require closure means associated therewith, but in the preferred embodiment both ports include the plugs 52*a*, 52*b***.

A stylet 56 is removably mounted within the hollow adapter 16, the tube 12 and the discharge portion 20. The stylet 56 includes a stylet plug 58 having wings 60 which may be employed as a handle to remove the stylet 56. A stylet wire 62 is permanently mounted at the higher proximal end 64 to the stylet plug 58. In the preferred embodiment, the stylet wire 62 is made from three smaller metal strands 66 which are wound about each other to create the stylet wire 62. The proximal end 64 of the stylet wire 62 is secured to the stylet plug 52 principally by means of an interference fit. The stylet wire 62 is bent at the proximal end 64 so as to engage opposite sides of the interior plug surface 68. In the preferred embodiment the proximal end 64 of the stylet wire 62 is heated before it is inserted into the plug 52, so that the proximal end 64 heats, softens and digs into the interior plug surface 68. The stylet plug 58 is snugly and removably mounted within the stylet port 42 of the adapter 16.

The stylet wire 62 extends substantially the entire length of the hollow tube 12. In the preferred embodiment illustrated, the distal end 70 of the wire 62 extends out the distal end 18 of the tube 12, into the discharge portion 20, almost touching the closed end 22. The maximum exterior diameter of the stylet wire 62 is less than the interior diameter of the hollow tube 12, as illustrated in the cross-sectional portions of FIG. 1. Thus, with the stylet 56 in place within the tube 12, the placement port 44 is in open fluid communication with the discharge apertures 24. The stylet 56 does not block fluid flow along this described path.

The prescribed products to be delivered through the feeding tube may include solid matter, usually in a liquid base. The word "fluid" is meant to include such product.

OPERATION

The naso-gastric feeding tube is used by first inserting the tube 10 into the naso-gastric system of a patient. The feeding tube 10 without the stylet 56 therein is too flexible to be inserted into the patient. However, with the stylet 56 therein, the feeding tube 10 is still flexible enough to make necessary bends and not produce trauma in the patient and is rigid enough to be inserted the necessary distance, which may be about three feet, for example, in an adult patient.

The slidable ring 32 may assist the operator in inserting the feeding tube 10 the proper distance. Before insertion of the feeding tube 10, the operator may hold the tube 10 above the patient's chest and make a rough approximation of the distance needed for the tube to reach the patient's stomach. The operator slides the slidable ring 32 along the tube 12 to mark the proper length of tube to be inserted into the patient.

Figure 3:
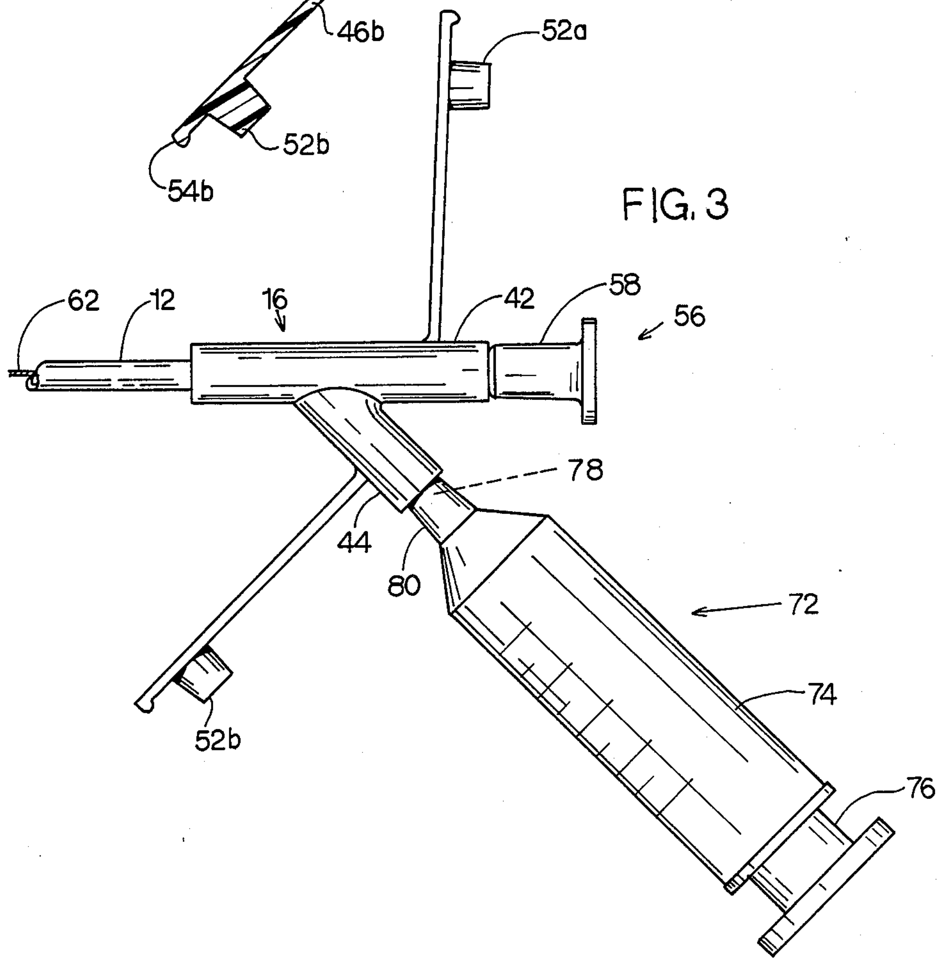
FIG. 3 is a fragmentary plan view illustrating the feeding tube placement procedure.

After the feeding tube 10 has been inserted into the patient, the operator, typically a nurse or doctor, must confirm that the distal end portion 30 of the feeding tube 10 is disposed properly in the right location within the patient. This typically would be the patient's stomach. This placement confirmation test may be performed by x-raying the patient to determine where the distal end portion 30 is located. Alternatively, and more commonly, the confirmation test is performed by means of a syringe 72. Referring to FIG. 3, the syringe 72 includes a hollow cylinder 74 with a piston 76 mounted therein. An outlet 78 is defined by a male luer fitting 80. The operator inserts the male luer fitting 80 into the placement port 44 of the adapter 16, after removal of the placement port plug **52*b***. The operator then performs one of two standard placement confirmation tests with the syringe.

In the first text, the syringe 72 is initially empty. The operator pulls back the piston 76, attempting to withdraw liquid into the syringe. If liquid from the stomach is withdrawn into the syringe 72, the operator knows that the feeding tube 10 has been properly placed within the patient.

The second test requires that air be in the syringe 72 when it is connected to the adapter 16. The operator injects the air or other fluid from the syringe, through the placement port 44 and the tube 12, around the stylet wire 62. The air exits the feeding tube 10 through the discharge apertures 24. While the air is being injected, the operator listen with a stethoscope to detect a "gurgling" or other audible mark which would indicate that the air has exited the feeding tube 10 at the patient's stomach.

If one of these two tests is positive, i.e. if proper placement is shown by removal of liquid from the stomach in the first test or the detection of the proper audible mark in the second test, the operator then removes the stylet 56. The stylet wire has not been previously removed for the placement test. If the placement confirmation test shows that proper placement has not been made, the operator need not remove the stylet wire. The operator simply holds the adapter 16 and moves the feeding tube 10 axially in one direction until he or she believes proper placement has been achieved. The operator then repeats one of the two placement confirmation tests with the syringe 72. Other placement tests, i.e. x-ray technique, may of course be used with the feeding tube 10 of the present invention.

Only when the placement confirmation test finally indicates that proper placement has been achieved does the operator withdraw the stylet 56 from the feeding tube. The stylet is then discarded.

Figure 4:
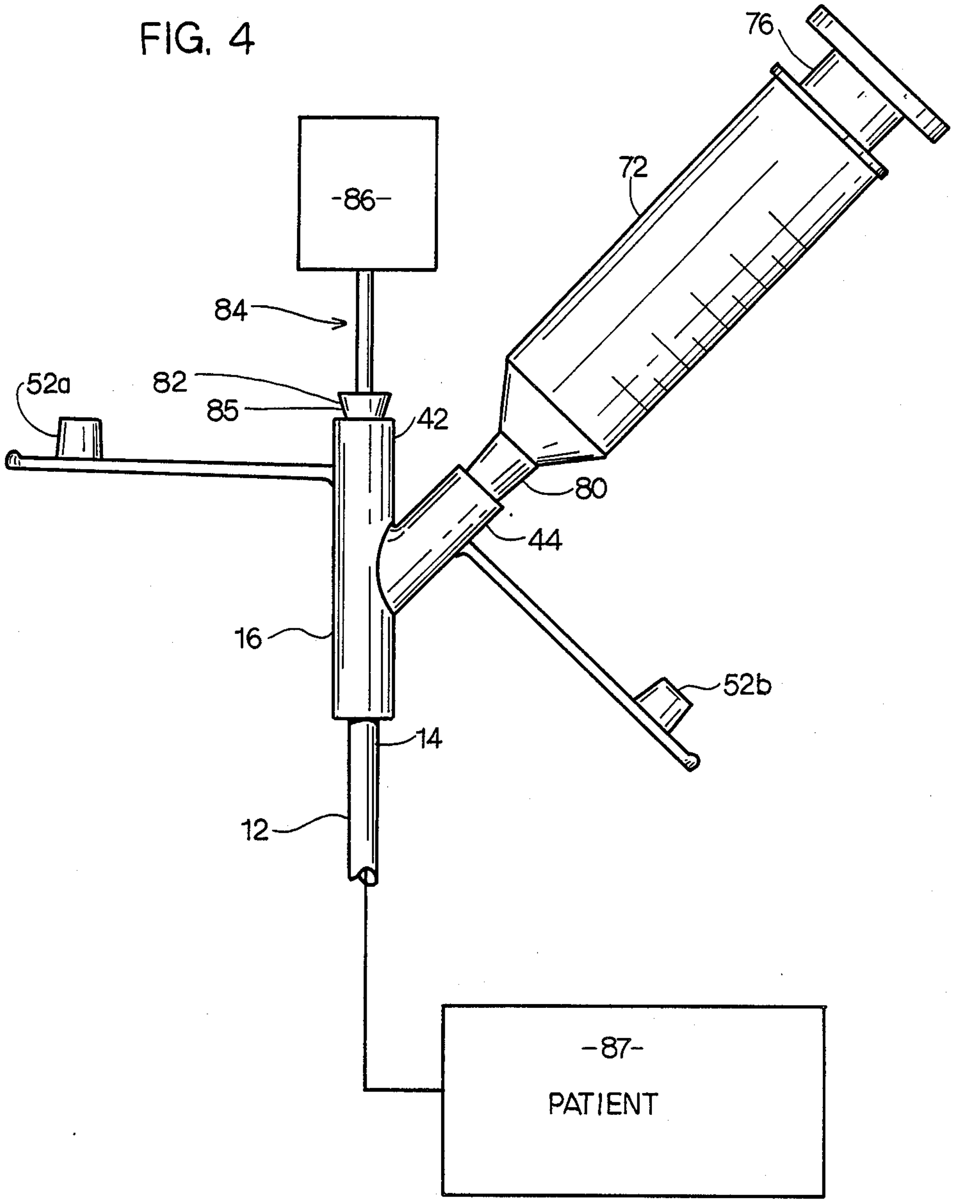
FIG. 4 is a partially schematic view illustrating delivery of a second prescribed product through the feeding tube, to a patient.

The operator attaches one of the stylet and placement ports 42, 44 to the distal end 82 of an enteral administration set 84 shown schematically in FIG. 4. The enteral set distal end 82 is typically a male luer adapter 85 which may be snugly mounted within the stylet port 42 or the placement port 44. In the preferred embodiment of the invention, the hollow adapter 16 has a "Y" type construction with the stylet port 42 extending straight from the proximal end 14 of the tube 12. The placement port 44 extends to the side in the other leg of the Y. In the preferred embodiment of the method of the invention, it is the stylet port 42 which is attached to the distal end 82 of the enteral administration set 84, but of course this is not necessary. Also, while it is believed that the present construction provides for easier movement of the stylet, the stylet and placement ports 42, 44 may be reversed. Furthermore, the adapter 16 may include a different configuration. For example, the ports 42, 44 may be disposed perpendicular to each other; however, it is believed that the Y construction works best in delivering two or more prescribed products to the patient 87.

Once one of the ports 42, 44 is secured to the enteral administration set 84, the operator closes the other of the ports 42, 44. In the preferred embodiment, after securing the stylet port 42 to the set 84, the operator closes the placement port 44 by inserting the plug **52*b*** therein.

In addition to providing the above-described advantages of performing the placement test without removing the stylet, eliminating the potential requirement of reinserting the stylet, the naso-gastric feeding tube 10 of the present invention permits subsequent, immediate delivery of a second prescribed product in virtually undiluted form.

As illustrated in FIG. 4, while the first prescribed product is being delivered from the source container 86, through the set 84 and feeding tube 10 into the patient, a second prescribed product may be delivered. If it is the stylet port 42 which is connected to the set 84, the operator removes the plug **52*b* from the placement port 44 and connects a syringe 72 or other delivery device to the tube 10 at the placement port 44. The syringe 72 may contain a drug, vitamins, or any other second prescribed product. The operator simply pushes the piston 76, expressing the syringe contents into the tube 12. The syringe 72 is removed and the placement port 44 is reclosed with the plug 52*b*. During delivery of the second prescribed product, the delivery of the first prescribed product need not be interrupted because the feeding tube 10 need not be disconnected from the administration set 84. Subsequent prescribed products may also be delivered to the patient in this manner, by removing the plug 52*b***.

While a preferred structure for a feeding tube and preferred methods for placing a feeding tube and for delivering two or more prescribed products have been described in detail herein and illustrated in the accompanying drawings, it will be evident that various further modifications are possible without departing from the scope of the invention.

What is claimed is:

1. A naso-gastric feeding tube comprising:

(A) a flexible, hollow tube having an open proximal end and a distal end;

(B) a discharge aperture defined near said distal end, in communication with the interior of said hollow tube;

(C) a hollow adapter permanently mounted on said open proximal end, the interior of said adapter being in open communication with the interior of the hollow tube, said adapter further including a stylet port and a placement port;

(D) at least one of said stylet port and said placement port including closure means associated therewith for closing said one port;

(E) a stylet including:

(i) a stylet plug removably mounted in said stylet port, and (ii) a stylet wire permanently mounted at its proximal end to said stylet plug and extending substantially the entire length of said hollow tube, within said hollow tube;

(F) the maximum exterior diameter of said stylet wire being sufficiently less than the interior diameter of said hollow tube, so that said placement port is in open fluid communication with said discharge aperture so that fluid may be withdrawn through said discharge aperture through said placement port while said stylet wire is in said tube; and (G) said stylet port and said placement port having means for simultaneously receiving separate products for discharge through said discharge aperture when said stylet is removed from said tube.

2. A method for correctly positioning a naso-gastric feeding tube within a patient, and subsequently feeding a patient prescribed products, the steps comprising:

(A) providing a naso-gastric feeding tube comprising:

(i) a flexible, hollow tube having an open proximal end and a distal end;

(ii) a discharge aperture defined near said distal end, in communication with the interior of said hollow tube;

(iii) a hollow adapter permanently mounted on said open proximal end, the interior of said adapter being in open communication with the interior of the hollow tube, said adapter further including a stylet port and a placement port;

(iv) at least one of said stylet port and said placement port including closure means associated therewith for closing said one port;

(v) a stylet including (a) a stylet plug removably mounted in said stylet port, and (b) a stylet wire permanently mounted at its proximal end to said stylet plug and extending substantially the entire length of said hollow tube, within said hollow tube; and (vi) the maximum exterior diameter of said stylet wire being less than the interior diameter of said hollow tube, so that said placement port is in open fluid communication with said discharge aperture;

(B) inserting the naso-gastric tube into the naso-gastric system of the patient;

(C) with the stylet remaining in the stylet port and the tube, testing for proper feeding tube placement by one of (i) injecting fluid by stringe through the tube around the stylet from the placement port in communication with the interior of the tube and listening for an audible mark indicating proper feeding tube placement, and (ii) attempting to withdraw liquid by syringe through the feeding tube and placement port, indicating proper feeding tube placement;

(D) repeating said testing step until proper feeding tube placement is indicated;

(E) after said testing step indicates proper feeding tube placement, withdrawing the stylet from the hollow tube and adapter; and (F) securing at least one of the stylet port and placement port to a source of first prescribed product to be administered to the patient through the tube.

3. The method as in claim 2, the steps further comprising:

(A) delivering the first prescribed product to the patient through one of said stylet and placement port;

(B) during said delivery step, without disconnecting the tube from the source, delivering a second prescribed product through the other of said stylet and placement port and the hollow tube to the patient.

4. The method as in claim 3, the steps further comprising: after said delivery of a second prescribed product through said other port, closing said other port.

* * * * *